United States Patent
Sedai et al.

(10) Patent No.: US 11,191,492 B2
(45) Date of Patent: Dec. 7, 2021

(54) EARLY DETECTION AND MANAGEMENT OF EYE DISEASES BY FORECASTING CHANGES IN RETINAL STRUCTURES AND VISUAL FUNCTION

(71) Applicants: International Business Machines Corporation, Armonk, NY (US); New York University, New York, NY (US)

(72) Inventors: Suman Sedai, Melbourne (AU); Bhavna Josephine Antony, Melbourne (AU); Rahil Garnavi, Melbourne (AU); Hiroshi Ishikawa, New York, NY (US)

(73) Assignees: International Business Machines Corporation, Armonk, NY (US); New York University, New York, NY (US)

( * ) Notice: Subject to any disclaimer, the term of this patent is extended or adjusted under 35 U.S.C. 154(b) by 85 days.

(21) Appl. No.: 16/251,167

(22) Filed: Jan. 18, 2019

(65) Prior Publication Data
US 2020/0229770 A1    Jul. 23, 2020

(51) Int. Cl.
*A61B 5/00* (2006.01)
*A61B 3/107* (2006.01)
*A61B 3/10* (2006.01)

(52) U.S. Cl.
CPC ............ *A61B 5/7275* (2013.01); *A61B 3/102* (2013.01); *A61B 3/107* (2013.01)

(58) Field of Classification Search
CPC ........ A61B 5/7275; A61B 3/102; A61B 3/107
See application file for complete search history.

(56) References Cited

U.S. PATENT DOCUMENTS

| | | | | |
|---|---|---|---|---|
| 7,782,464 | B2* | 8/2010 | Mujat | G06T 7/149 356/479 |
| 8,879,813 | B1* | 11/2014 | Solanki | G06T 5/008 382/128 |
| 9,423,237 | B2* | 8/2016 | Milner | G01B 9/02091 |
| 9,483,866 | B2* | 11/2016 | Stetson | A61B 5/0066 |
| 9,775,506 | B2 | 10/2017 | Burlina et al. | |
| 9,836,849 | B2* | 12/2017 | Dickrell, III | G06T 7/168 |
| 10,123,701 | B2* | 11/2018 | Shau | A61B 3/165 |
| 10,198,832 | B2* | 2/2019 | De Fauw | G06T 7/0012 |
| 10,368,734 | B2* | 8/2019 | Durbin | A61B 3/102 |
| 10,468,142 | B1* | 11/2019 | Abou Shousha | A61B 3/0025 |
| 2007/0058856 | A1* | 3/2007 | Boregowda | G06K 9/3258 382/159 |
| 2011/0021319 | A1* | 1/2011 | Nissila | A61B 5/222 482/8 |

(Continued)

OTHER PUBLICATIONS

Mel, et al. "The NIST Definition of Cloud Computing". Recommendations of the National Institute of Standards and Technology. Nov. 16, 2015.

*Primary Examiner* — Carl H Layno
*Assistant Examiner* — Manolis Pahakis
(74) *Attorney, Agent, or Firm* — Joseph Petrokaitis, Esq.; McGinn I.P. Law Group, PLLC.

(57) ABSTRACT

A retinal structure and function forecasting method, system, and computer program product include producing an enriched feature representation of clinical measurements and clinical data combined with optical coherence tomography (OCT) data, training a forecasting model with the enriched feature representation, and forecasting a retinal structure at a forecast date based on the trained forecasting model.

17 Claims, 9 Drawing Sheets

(56) References Cited

U.S. PATENT DOCUMENTS

| | | | |
|---|---|---|---|
| 2011/0190657 A1* | 8/2011 | Zhou | G16H 50/70 600/558 |
| 2012/0257164 A1* | 10/2012 | Zee | A61B 3/12 351/206 |
| 2012/0287401 A1* | 11/2012 | Bizios | A61B 3/0025 351/206 |
| 2013/0114041 A1* | 5/2013 | Iftekharuddin | G06K 9/6247 351/206 |
| 2013/0308824 A1* | 11/2013 | Leung | G06T 7/0016 382/103 |
| 2014/0112562 A1* | 4/2014 | Yamakawa | A61B 3/0041 382/131 |
| 2015/0019136 A1* | 1/2015 | Medeiros | A61B 3/1005 702/19 |
| 2015/0124216 A1* | 5/2015 | Abramoff | A61B 3/0025 351/206 |
| 2016/0174830 A1* | 6/2016 | Rubin | A61B 3/102 351/206 |
| 2016/0232324 A1* | 8/2016 | Liu | A61B 5/4842 |
| 2017/0156582 A1* | 6/2017 | Ehlers | G06T 7/0012 |
| 2017/0202448 A1* | 7/2017 | Mwanza | A61B 5/7275 |
| 2017/0208245 A1* | 7/2017 | Castillo | H04N 1/2104 |
| 2017/0213126 A1* | 7/2017 | Hammond | G06N 5/04 |
| 2018/0004899 A1* | 1/2018 | Takeda | G16H 40/20 |
| 2018/0047159 A1* | 2/2018 | Schlegl | A61B 3/102 |
| 2018/0070814 A1* | 3/2018 | Mikaelian | A61B 3/024 |
| 2018/0084988 A1* | 3/2018 | Chakravorty | A61B 3/102 |
| 2018/0096259 A1* | 4/2018 | Andrews | G06T 7/251 |
| 2018/0132725 A1* | 5/2018 | Vogl | A61B 3/0025 |
| 2018/0160894 A1* | 6/2018 | Gupta | A61B 5/7264 |
| 2018/0292824 A1* | 10/2018 | Kazemi | G08G 1/0112 |
| 2018/0368679 A1* | 12/2018 | An | A61B 3/0025 |
| 2019/0043193 A1* | 2/2019 | Odaibo | G06K 9/00617 |
| 2019/0110681 A1* | 4/2019 | Leung | A61B 3/102 |
| 2019/0110753 A1* | 4/2019 | Zhang | G16H 50/20 |
| 2019/0259163 A1* | 8/2019 | Mao | G06K 9/36 |
| 2019/0272631 A1* | 9/2019 | Shemonski | A61B 3/102 |
| 2020/0075155 A1* | 3/2020 | Huang | G06T 7/10 |
| 2020/0077883 A1* | 3/2020 | Ehlers | A61B 5/004 |
| 2020/0085382 A1* | 3/2020 | Taerum | G06T 7/30 |
| 2020/0242763 A1* | 7/2020 | Bhuiyan | G06T 7/12 |
| 2020/0288971 A1* | 9/2020 | Huang | G06T 7/168 |
| 2021/0082116 A1* | 3/2021 | Mao | A61B 3/0025 |
| 2021/0158525 A1* | 5/2021 | Iwase | G06T 7/97 |

* cited by examiner

EARLY DETECTION AND MANAGEMENT OF EYE DISEASES BY FORECASTING CHANGES IN RETINAL STRUCTURES AND VISUAL FUNCTION

BACKGROUND

The present invention relates generally to a retinal structure and function forecasting method, and more particularly, but not by way of limitation, to a system, method, and computer program product for early detection and management of eye diseases by forecasting changes in retinal structures and visual function parameters.

Glaucoma is a chronic ophthalmic disease characterized by progressive irreversible retinal ganglion cell (RGC) layer and retinal nerve fiber layer (RNFL) loss, associated with accompanying optic nerve abnormalities and corresponding visual field changes.

Conventionally, glaucoma is the leading cause of irreversible blindness worldwide. A meta-analysis of fifty population-based studies estimated the prevalence of glaucoma to be 3.54% amongst individuals between 40-80 years of age (95% confidence interval, 2.09-5.82). Therefore, glaucoma has a significant economic burden, both direct and indirect. Direct costs include ocular hypotensive medications, specialist visits, glaucoma-related procedures and surgeries, low vision programs (including guide dogs), and nursing home care. Indirect costs include lost productivity.

Diagnosis of glaucoma is difficult as a multitude of factors may be required to diagnose glaucoma including intraocular pressure (IOP), changes to the optic disc (visible in fundus photographs), and loss in the retinal nerve fibers and ganglion cells (obtained from optical coherence tomography (OCT)). The only irrefutable criterion is progressive glaucomatous visual field loss (e.g., an arcuate bundle defect, nasal step, paracentral scotoma, and an altitudinal defect) distinct from neurological field defects or non-progressive defects that can mimic glaucoma. Even this is not always straightforward due to high inter-visit variability of perimeter and the need to show progression of the same deficit, which can take several years.

Conventional diagnosis techniques sought to predict five-year risk of progression of patients with ocular hypertension to primary open angle glaucoma (POAG). A glaucoma progression risk calculator is used by the conventional techniques that combines the longitudinal data from the Ocular Hypertension Study (OHTS) and European Glaucoma Prevention Study (EGPS). These included data such as age, IOP, OCT, vertical cup to disc ratio (CDR), and pattern standard deviation of visual field test. When the point system estimates greater than 15% chance of conversion to glaucoma in the next five-years, the conventional prediction model provides evidence of when to initiate therapy selectively (instead of treating every case of high IOP).

SUMMARY

Thus, the inventors have identified a need in the art for an improved technique for management of eye diseases such as glaucoma by forecasting changes in retinal structures, such as the retinal nerve fibre and ganglion cell layers, as well as visual function parameters, such as mean deviation (MD) and visual field index (VFI) from Humphrey visual field tests.

In an exemplary embodiment, the present invention provides a computer-implemented retinal structure and function forecasting method, the method including producing an enriched feature representation of clinical measurements and clinical data combined with optical coherence tomography (OCT) data, training a forecasting model with the enriched feature representation, and forecasting changes in retinal structures and visual function parameters at a forecast date based on the trained forecasting model.

One or more other exemplary embodiments include a computer program product and a system, based on the method described above.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

The invention will now be described with reference to FIGS. 1-9, in which like reference numerals refer to like parts throughout. It is emphasized that, according to common practice, the various features of the drawings are not necessarily to scale. On the contrary, the dimensions of the various features can be arbitrarily expanded or reduced for clarity.

Figure 1:
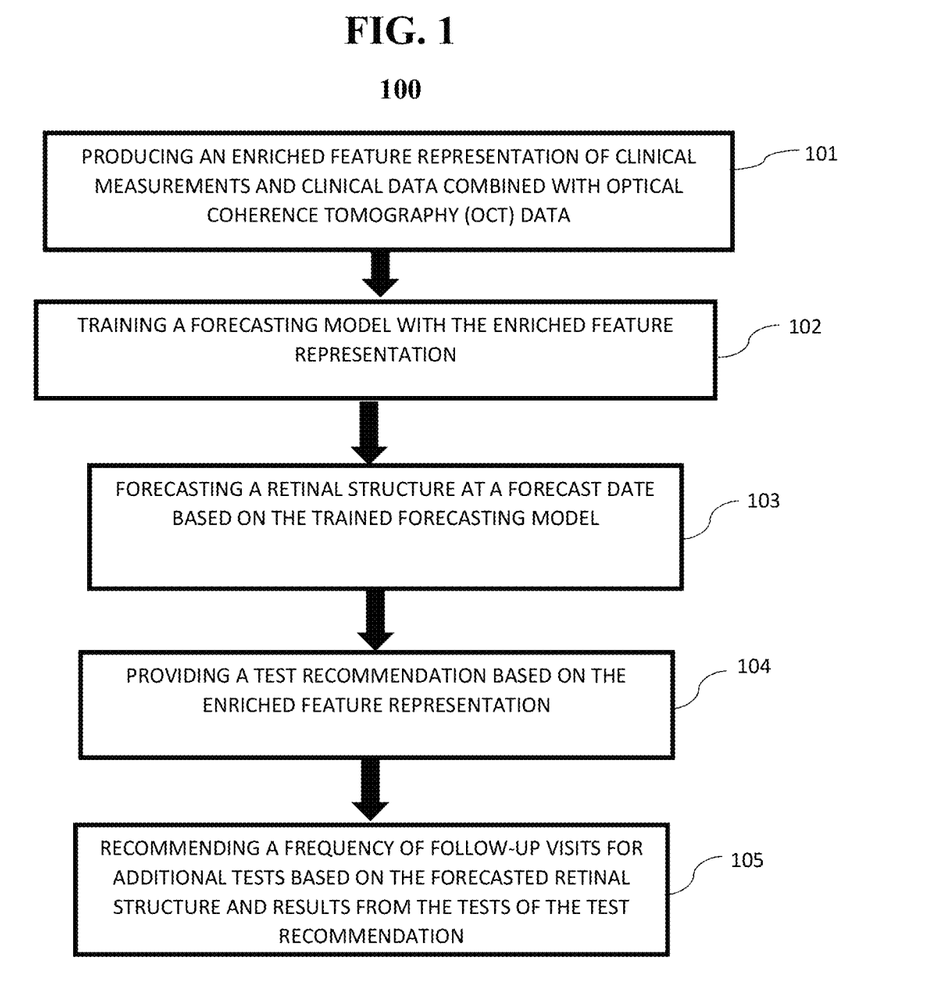
FIG. 1 exemplarily shows a high-level flow chart for retinal structure and visual field change forecasting method 100 according to an embodiment of the present invention.

By way of introduction of the example depicted in FIG. 1, an embodiment of a retinal structure and function forecasting method 100 according to the present invention can include various steps for early detection and management of eye diseases by forecasting changes in retinal optic nerve head.

Figure 7:
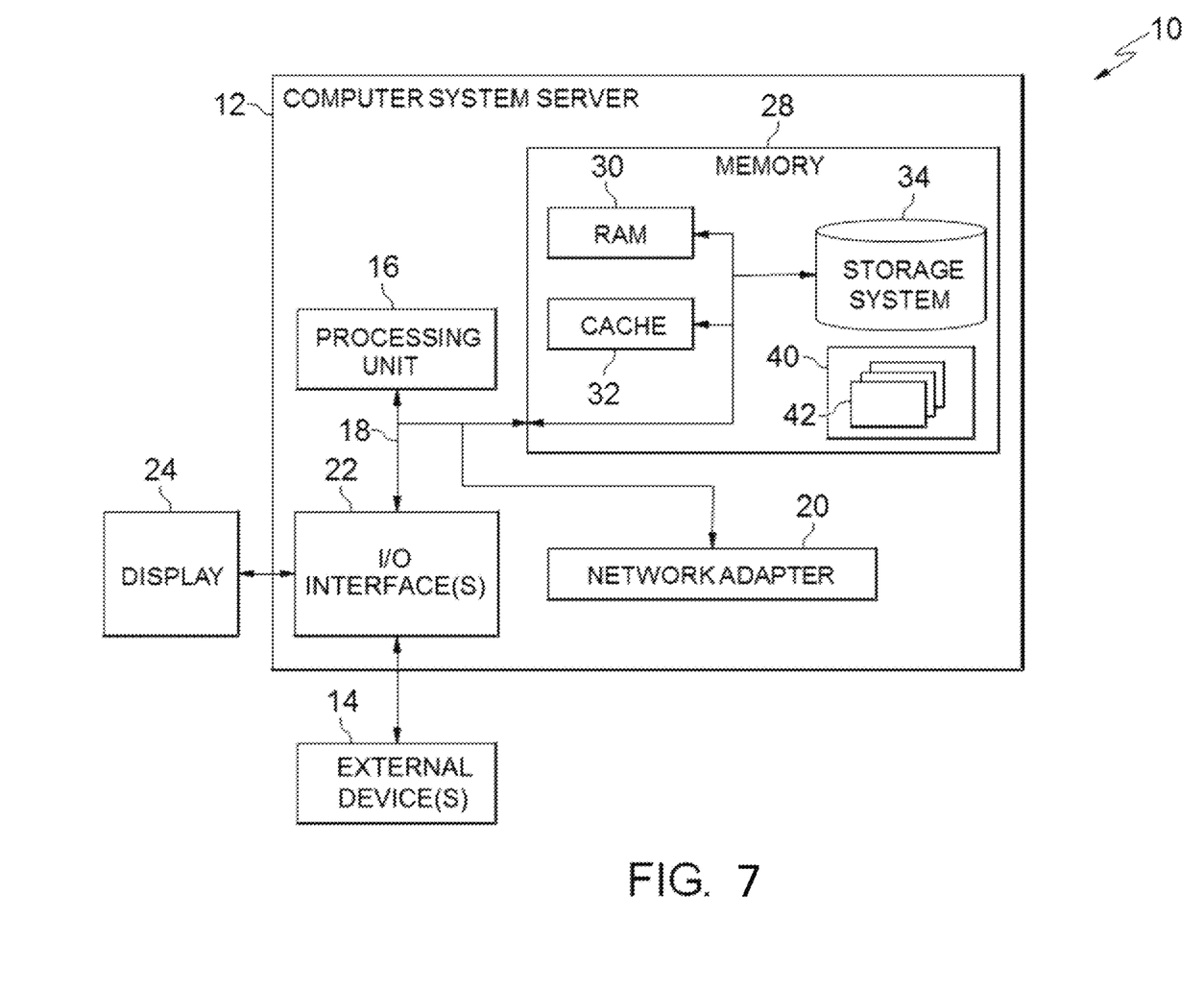
FIG. 7 depicts a cloud-computing node 10 according to an embodiment of the present invention.
Figure 8:
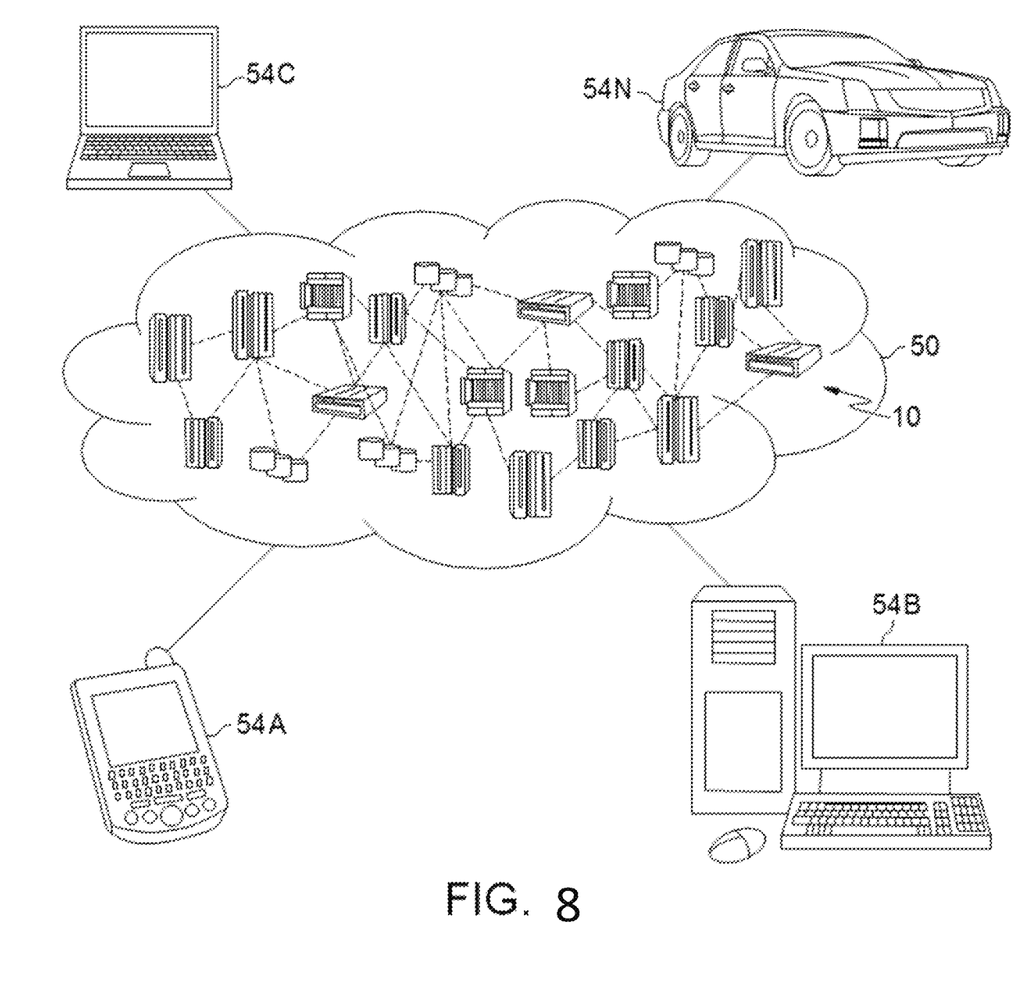
FIG. 8 depicts a cloud-computing environment 50 according to an embodiment of the present invention.
Figure 9:
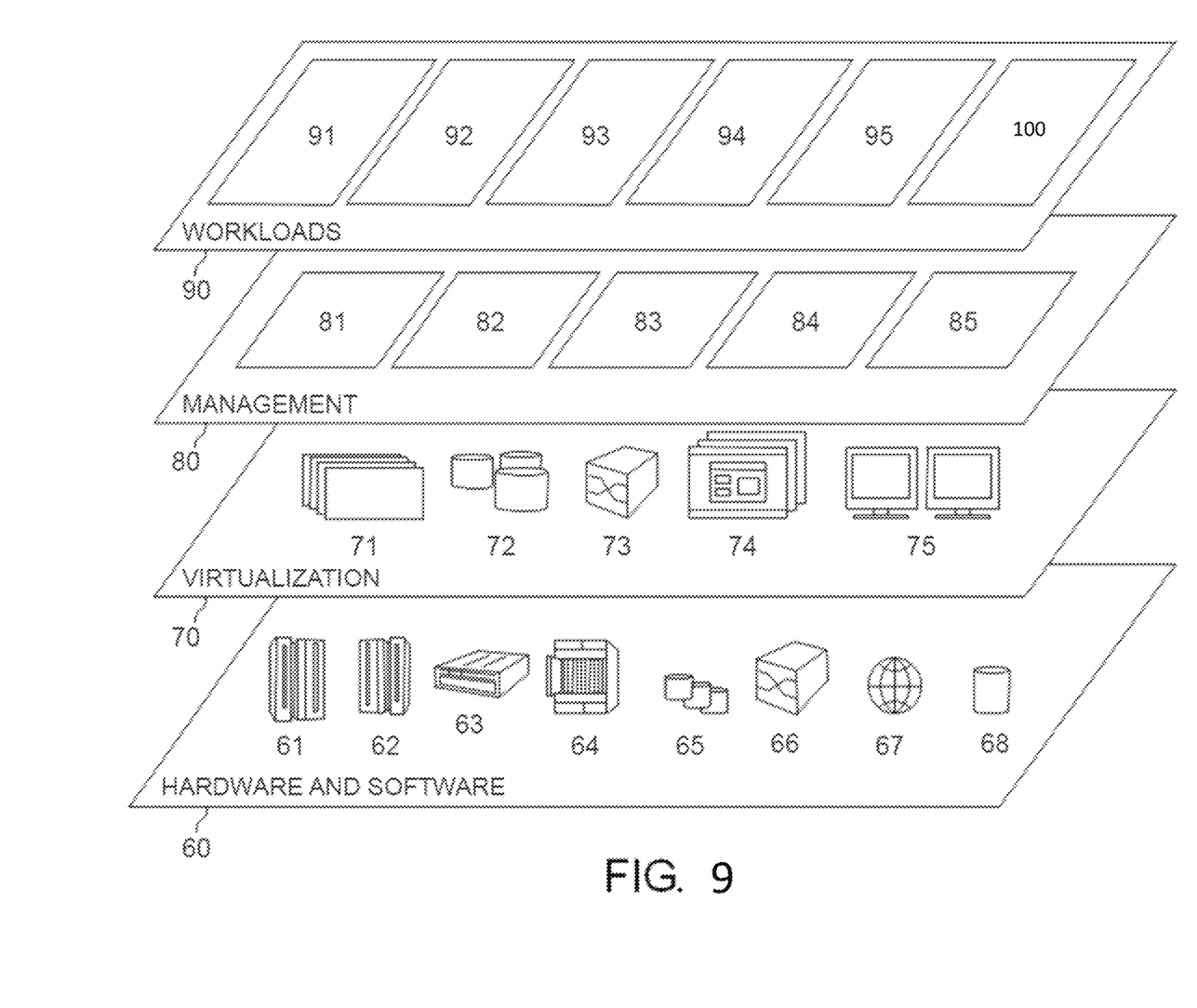
FIG. 9 depicts abstraction model layers according to an embodiment of the present invention.

By way of introduction of the example depicted in FIG. 7, one or more computers of a computer system 12 according to an embodiment of the present invention can include a memory 28 having instructions stored in a storage system to perform the steps of FIG. 1.

Although one or more embodiments may be implemented in a cloud environment 50 (e.g., FIG. 9), it is nonetheless understood that the present invention can be implemented outside of the cloud environment.

The method 100 may act in a more sophisticated and useful fashion, and in a cognitive manner while giving the impression of mental abilities and processes related to knowledge, attention, memory, judgment and evaluation, reasoning, and advanced computation. That is, a system is said to be "cognitive" if it possesses macro-scale properties—perception, goal-oriented behavior, learning/memory and action—that characterize systems (i.e., humans) that all agree are cognitive.

Cognitive states are defined as functions of measures of a host's total behavior collected over some period of time from at least one personal information collector (e.g., including musculoskeletal gestures, speech gestures, eye movements, internal physiological changes, measured by imaging circuits, microphones, physiological and kinematic sensors in a high dimensional measurement space, etc.) within a lower dimensional feature space. In one exemplary embodiment, certain feature extraction techniques are used for identifying certain cognitive and emotional traits. Specifically, the reduction of a set of behavioral measures over some period of time to a set of feature nodes and vectors, corresponding to the behavioral measures' representations in the lower dimensional feature space, is used to identify the emergence of a certain cognitive state(s) over that period of time. One or more exemplary embodiments use certain feature extraction techniques for identifying certain cognitive states. The relationship of one feature node to other similar nodes through edges in a graph corresponds to the temporal order of transitions from one set of measures and the feature nodes and vectors to another. Some connected subgraphs of the feature nodes are herein also defined as a "cognitive state". The present application also describes the analysis, categorization, and identification of these cognitive states further feature analysis of subgraphs, including dimensionality reduction of the subgraphs, for example graphical analysis, which extracts topological features and categorizes the resultant subgraph and its associated feature nodes and edges within a subgraph feature space.

Referring to FIG. 1, in step 101, an enriched feature representation of clinical measurements and clinical data combined with optical coherence tomography (OCT) data is produced. A new Convolution Neural Network (CNN) is used with augmented features where the measurements and clinical data (e.g., intra-ocular pressure (IOP), visual field test, patient prior history, etc.) is combined with the raw OCT cubes using the CNNs to produce the enriched feature representation. The enriched feature representation captures the relevant features from OCT as well as clinical feature and patient history. The feature learning is performed using single visit by optimizing the CNN to predict the layer parameters for the next visit conditioned on the clinical measurement and the time interval.

It is noted that 'enriched feature representation means' that the feature representation includes rich data. 'Rich data' means the combined feature representation, that encapsulates relevant information from the images of the retina (such as OCT cubes, fundus images, fluorescence angiogram images) as well as existing clinical measurements such as Intra-ocular pressure, visual field test and patient history of pre-existing conditions such as diabetes and hypertension and family history of eye diseases.

In step 102, a forecasting model is trained with the enriched feature representation. The enriched feature representation from multiple visits is used to train the forecasting model. The forecasting model may be a machine-learning model that takes the enriched feature representations at a single visit (or multiple visits) and a time interval between the forecast date and the latest visit and predicts the structural parameters (e.g., retinal structure) at the forecast date. The forecasting model may be built using existing machine learning algorithms such as deconvolution neural networks (i.e., for thickness map 2-dimensional map prediction) or a support vector machine technique for thickness values of the retina predictions. The forecasting model may be optimized using a mean squared error loss function to predict the retinal nerve fiber layer (RNFL) thickness parameters and/or RNFL 2-dimensional thickness map for the future visit.

In step 103, a retinal structures or visual function is forecasted at a future date using the trained forecasting model. For example, the output of the forecasting model can be cumpapillary retinal nerve fibre layer (cpRNLF) structure which is a widely used clinical biomarker for glaucoma management. This captures the expected changes in a patient's retinal optic nerve head. In another example, the output of the forecasting model can be visual function parameter such as mean deviation and visual field index which capture the degree of vision of the subject. The forecast may be based on the multimodal information, such as raw OCT image, clinical measurements and patient history as described above in 0028.

In step 104, a test recommendation is provided based on the enriched feature representation. That is, tests such as a visual field (VF) test, IOP test, OCT-Angiography test, a corneal angle assessment (CAA), corneal thickness measurements (CTM), etc. can be recommended according to the measurements and clinical data combined with the raw OCT cubes.

In step 105, a frequency of follow-up visits is recommended for additional tests based on the forecasted retinal structure and results from the tests of the test recommendation. That is, in step 105, a frequency of follow-up visits is recommended for the patient and additional tests (e.g., early intervention for rapidly deteriorating Glaucoma patients, faster follow-up for rapidly progressing patients) based on test observations and the forecasted structure.

It is noted that the forecasting in step 103 may forecast a predicted change in retinal structure at a specific time. Thereby, in step 104, the testing can be recommended at the predetermined time(s) to provide early treatment to predicted changes in the retinal structure.

Figure 2:
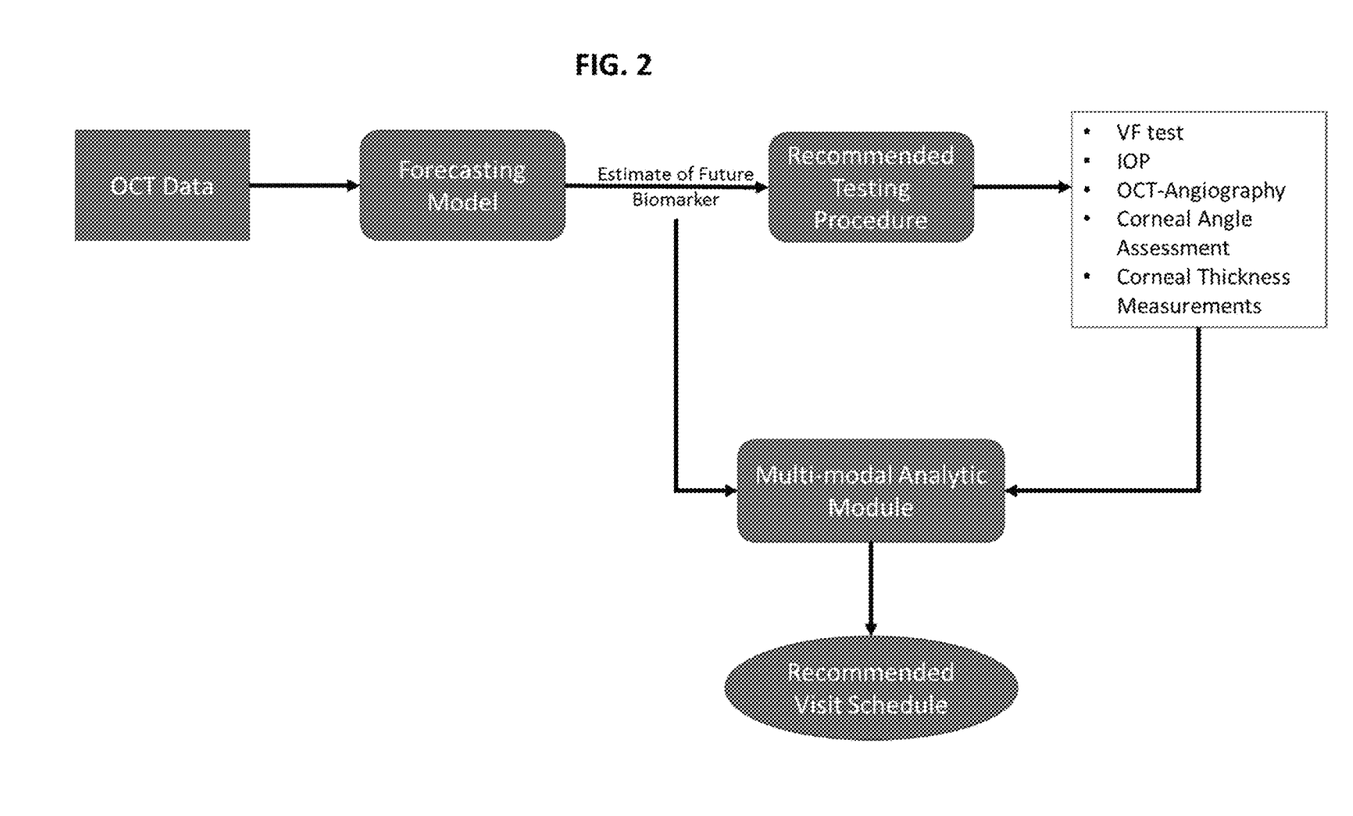
FIG. 2 exemplarily depicts a flow chart of the method 100 according to an embodiment of the present invention.

For example, FIG. 2 exemplarily depicts a flow chart according to the method 100. Based on OCT data, a forecasting model is created which is used to predict future biomarkers (e.g., changes in the retinal structure). Based on these, testing procedures are recommended and then the tests combined with the predicted change in the retinal structure are used in a multimodal analytic module to create a recommended visit schedule for a patient to obtain optimal treatment.

That is, FIG. 2 exemplarily depicts a flow for a management for eye diseases such as glaucoma by forecasting the retinal structures. The process flow includes a forecast for the retinal structures in the future visits, which is better (i.e., more reliable) than the state of the art. Based on that, the method provides a test recommendation from a set of tests such as visual field test, angiography, etc. The observation from the test and the forecasted structure is then used to plan the follow-up visit of the patient. This technique also seeks to be applicable to a broader range of glaucoma suspects, not just those with ocular hypertension (for example, patients with large cup-to-disc ratio (CDRs) but normal IOPs).

The flow chart as shown in FIG. 2 includes a test recommendation and a visit scheduling technique by forecasting the structural changes in retinal optic nerve head. The retinal structure forecasting (e.g., forecasting changes in retinal optic nerve head for early detection of eye diseases) uses multimodal information such as raw OCT image, clinical measurements and patient history. As a result of the predictions, the method may recommend early intervention for rapidly deteriorating glaucoma patients. At the same time, the invention suggests the follow-up time based how much fast they are progressing.

Figure 3:
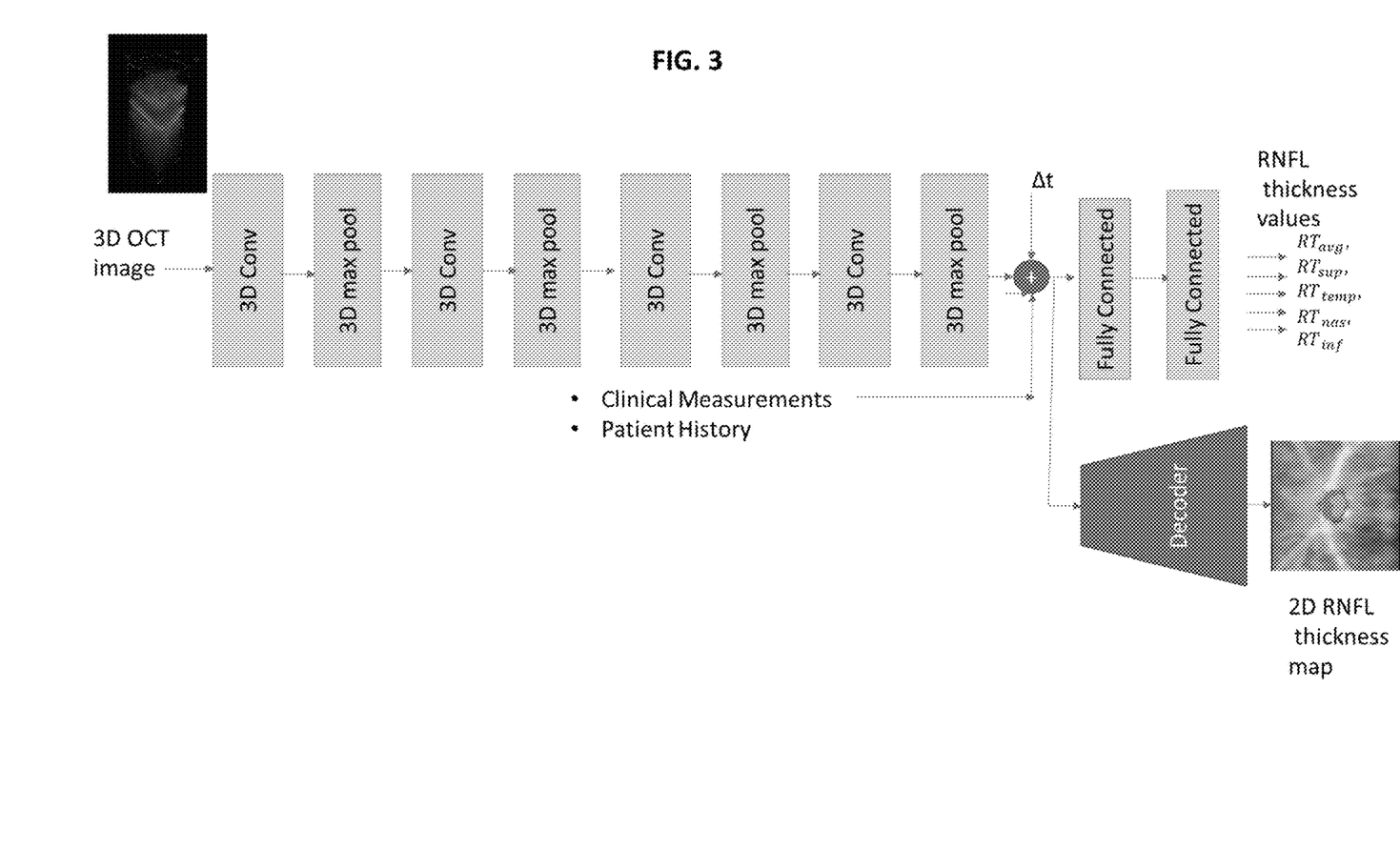
FIG. 3 exemplarily depicts a technique for a thickness map prediction from a single visit to a doctor according to an embodiment of the present invention.

For example, FIG. 3 exemplarily shows how 3D convolutional neural network combines the 3D OCT image with clinical measurements and patient history information to forecast the RNFL thickness values and 2D RNFL thickness map from a single visit. The used the network can also be trained to forecast the visual functions such as mean deviation and visual field index.

Figure 4:
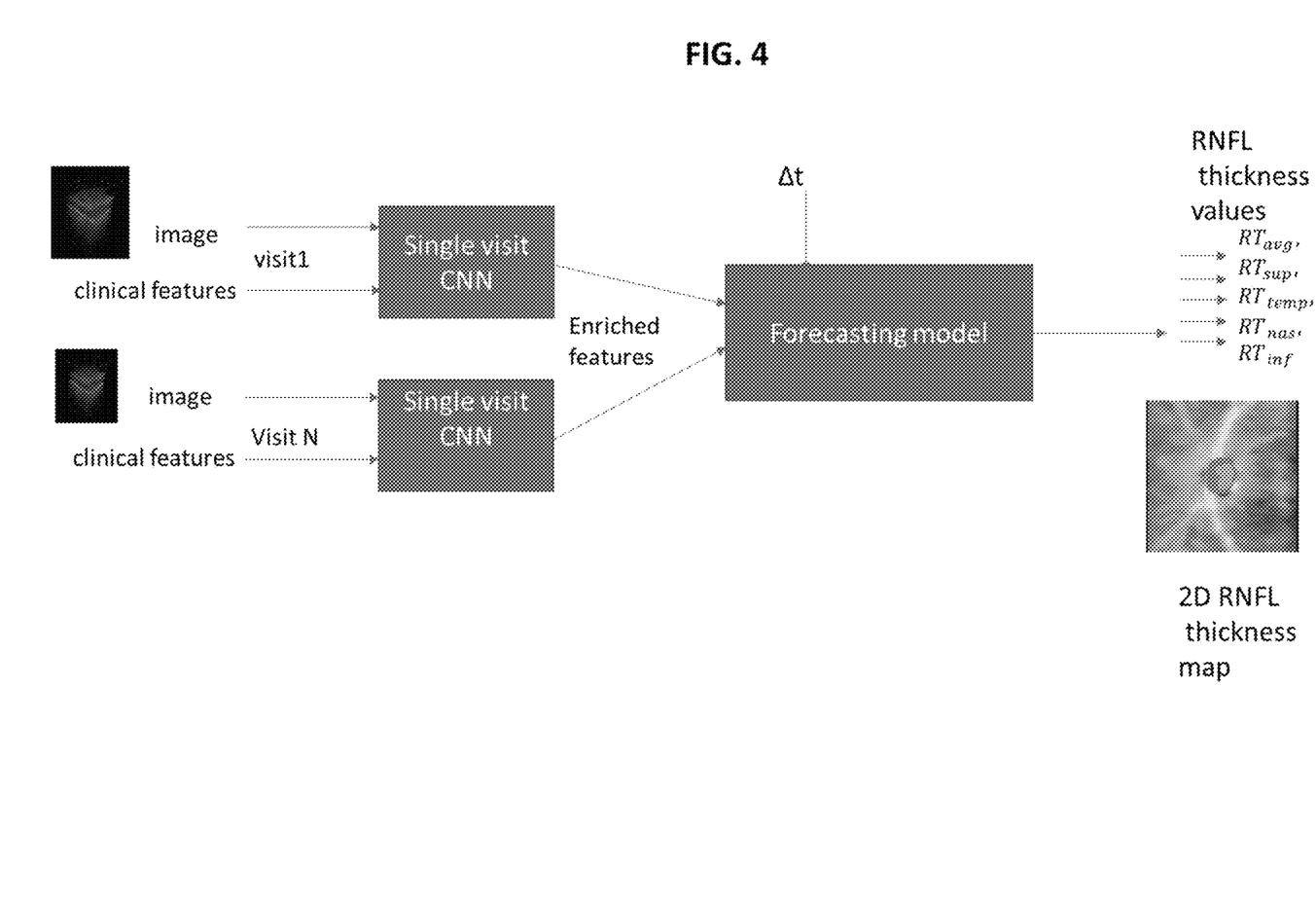
FIG. 4 exemplarily depicts a technique for a thickness map prediction from multiple visits to the doctor according to an embodiment of the present invention.

FIG. 4 shows how the multiple visit images and clinical measurements are used with single visit CNN (FIG. 3) to forecast the RNFL thickness values and RNFL thickness map for the future visit. This method can be applied to forecast the visual functions such as mean deviation and visual field index.

Figure 5:
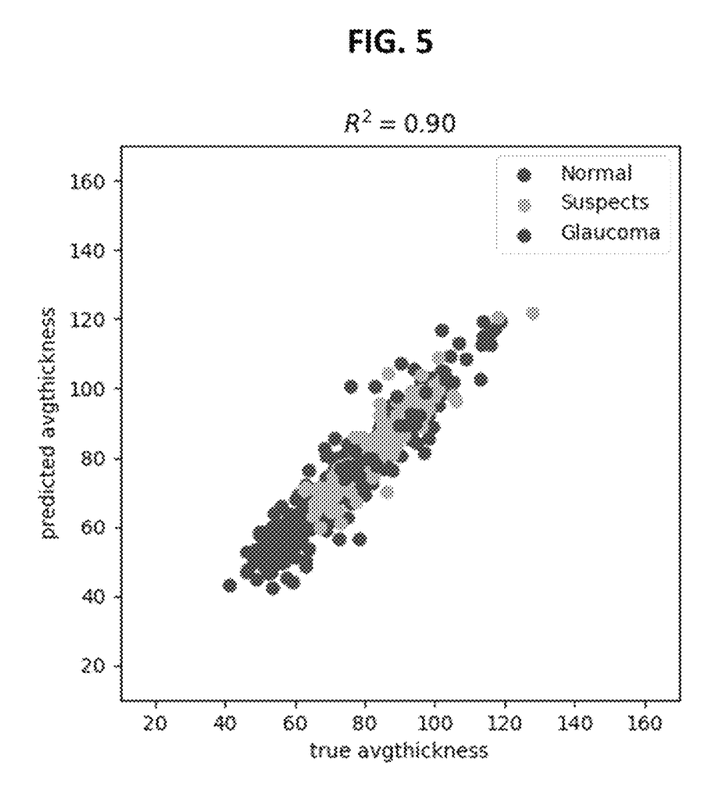
FIG. 5 exemplarily depicts a forecasting result using a conventional trend based technique.
Figure 6:
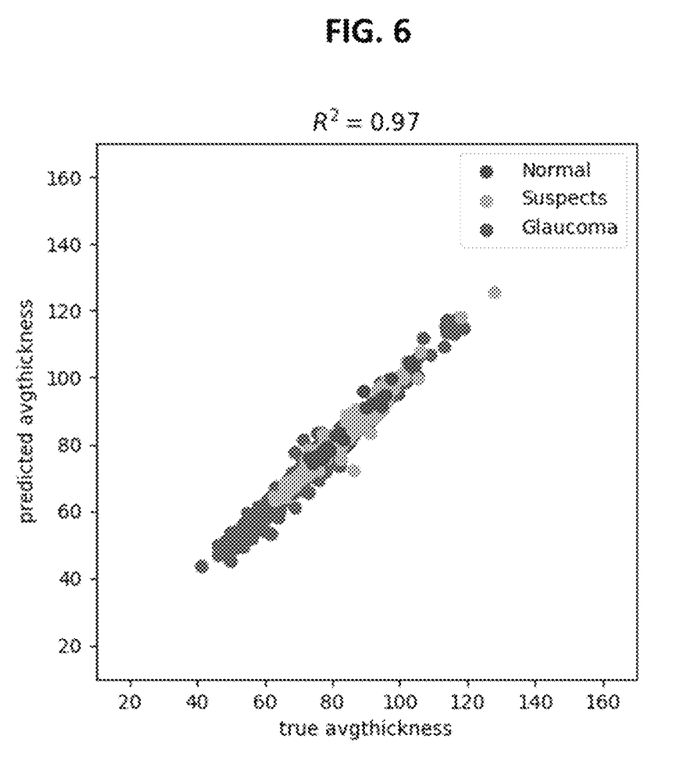
FIG. 6 exemplarily depicts a forecasting result using the method 100.

FIGS. 5-6 exemplarily depict results of conventional techniques and the method 100. As shown, the method 100 produces the forecasted RNFL thickness values that are more correlated (denoted by higher $R^2$ value) to the true future average RNFL thickness than the conventional technique.

Thus, the invention helps clinicians to choose a right test for early clinical intervention while providing cost saving in glaucoma management. Since glaucoma is irreversible, any delayed intervention is costly for both patients and government. Also, the invention assist clinicians in inter-visit planning (i.e., recommend when to visit next based on progression rate according to the change in retinal structure). Indeed, an optimized schedule of visits can be generated based on a specific patient's rate of glaucoma progression.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 3, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring now to FIG. 3, a computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further described below, memory 28 may include a computer program product storing one or program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may be adapted for implementation in a networking environment. In some embodiments, program modules 42 are adapted to generally carry out one or more functions and/or methodologies of the present invention.

Computer system/server 12 may also communicate with one or more external devices 14 such as a keyboard, a pointing circuit, other peripherals, such as display 24, etc., and one or more components that facilitate interaction with computer system/server 12. Such communication can occur via Input/Output (I/O) interface 22, and/or any circuits (e.g., network card, modem, etc.) that enable computer system/server 12 to communicate with one or more other computing circuits. For example, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Referring now to FIG. 4, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 4 are intended to be illustrative only and that computing nodes 10 and cloud computing environment 50 can communicate with any type of computerized circuit over any type of network and/or network addressable connection (e.g., using a web browser).

Referring now to FIG. 5, an exemplary set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and retinal structure and function forecasting method 100 in accordance with the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented retinal structure and function forecasting method, the method comprising:
   producing an enriched feature representation of clinical measurements and clinical data combined with optical coherence tomography (OCT) data including a current retinal structure, during a single office visit of a patient;
   training a forecasting model with the enriched feature representation produced during the single office visit; and
   forecasting a retinal structure at a forecast date and a change in the retinal structure at the forecast date from the current retinal structure based on the trained forecasting model.

2. The computer-implemented retinal structure and function forecasting method of claim 1, wherein the forecast model is trained by optimizing a convolution neural network to predict a layer parameter for a next appointment conditioned on a clinical measurement and a time interval.

3. The computer-implemented retinal structure and function forecasting method of claim 1, wherein the forecast model is further trained using a second visit after the single visit to a doctor by a patient by optimizing a convolution neural network to predict a layer parameter for a next appointments conditioned on a clinical measurement and a time interval.

4. The computer-implemented retinal structure and function forecasting method of claim 1, wherein the forecasting model is optimized using a mean-squared error loss function to predict a retinal nerve fiber layer (RNFL) thickness parameter at a future time.

5. The computer-implemented retinal structure and function forecasting method of claim 4, wherein the forecasting forecasts a change in the retinal structure based on the predicted RNFL thickness parameter.

6. The computer-implemented method of claim 1, implemented in a cloud-computing environment.

7. A computer program product for retinal structure and function forecasting, the computer program product comprising a non-transitory computer-readable storage medium having program instructions embodied therewith, the program instructions executable by a computer to cause the computer to perform:
   producing an enriched feature representation of clinical measurements and clinical data combined with optical coherence tomography (OCT) data including a current retinal structure, during a single office visit of a patient;
   training a forecasting model with the enriched feature representation produced during the single office visit; and
   forecasting a retinal structure at a forecast date and a change in the retinal structure at the forecast date from the current retinal structure based on the trained forecasting model.

8. The computer program product of claim 7, further comprising providing a test recommendation based on the enriched feature representation.

9. The computer program product of claim 8, further comprising recommending a frequency of follow-up appointments for additional tests based on the forecasted retinal structure and a result from the test of the test recommendation.

10. The computer program product of claim 7, wherein the forecasting forecasts a change in a retinal optic nerve head of the retinal structure for early detection of an eye disease.

11. The computer program product of claim 7, wherein the forecast model is trained by optimizing a convolution neural network to predict a layer parameter for a next appointment conditioned on a clinical measurement and a time interval.

12. The computer program product of claim 7, wherein the forecast model is further trained using a second visit after the single visit to a doctor by a patient by optimizing a convolution neural network to predict a layer parameter for a next appointments conditioned on a clinical measurement and a time interval.

13. The computer program product of claim 7, wherein the forecasting model is optimized using a mean-squared error loss function to predict a retinal nerve fiber layer (RNFL) thickness parameter at a future time.

14. The computer program product of claim 13, wherein the forecasting forecasts a change in the retinal structure based on the predicted RNFL thickness parameter.

15. A retinal structure and function forecasting system, the system comprising:
   a processor; and
   a memory, the memory storing instructions to cause the processor to perform:
      producing an enriched feature representation of clinical measurements and clinical data combined with optical coherence tomography (OCT) data including a current retinal structure, during a single office visit of a patient;
      training a forecasting model with the enriched feature representation produced during the single office visit; and
      forecasting a retinal structure at a forecast date and a change in the retinal structure at the forecast date from the current retinal structure based on the trained forecasting model.

16. The system of claim 15, further comprising providing a test recommendation based on the enriched feature representation.

17. The system of claim 15, configured to operate in a cloud-computing environment.

* * * * *